United States Patent [19]

Taylor

[11] Patent Number: 5,419,343
[45] Date of Patent: May 30, 1995

[54] ARTHROSCOPY DRAPE AND COLLECTION POUCH

[75] Inventor: Richard H. Taylor, Columbus, Miss.

[73] Assignee: Microtek Medical, Inc., Columbus, Miss.

[21] Appl. No.: 153,268

[22] Filed: Nov. 15, 1993

Related U.S. Application Data

[63] Continuation of Ser. No. 971,350, Nov. 4, 1992, abandoned, which is a continuation-in-part of Ser. No. 853,493, Mar. 18, 1992, abandoned.

[51] Int. Cl.⁶ .................... A61B 19/00; A61B 19/08
[52] U.S. Cl. ..................................... 128/849; 128/853
[58] Field of Search ............................ 128/849–856

[56] References Cited

U.S. PATENT DOCUMENTS

| | | | |
|---|---|---|---|
| 4,169,472 | 10/1979 | Morris | 128/854 |
| 4,196,723 | 4/1980 | Moose | 128/854 |
| 4,414,968 | 11/1983 | Amin | 128/853 |
| 4,462,396 | 7/1984 | Wichman | 128/853 |
| 4,489,720 | 12/1984 | Morris | 128/853 |
| 4,553,539 | 11/1985 | Morris | 128/854 |
| 4,559,937 | 12/1985 | Vinson | 128/853 |
| 4,974,604 | 12/1990 | Morris | 128/853 |
| 5,002,069 | 3/1991 | Thompson | 128/853 |
| 5,143,091 | 9/1992 | Patnode | 128/853 |

Primary Examiner—Michael A. Brown
Attorney, Agent, or Firm—Baker & Botts

[57] ABSTRACT

An arthroscopy drape is provided that has an open top collection pouch connected therewith. The pouch is connected adjacent to a fenestration or opening in the drape through which a patient's limb will extend for an arthroscopy procedure. Connection of the collection pouch to the drapery panel is provided over a relatively small area whereby articulation of the joint on which the procedure is being performed will have little if any effect on the position of the drapery panel relative to the patient and operating equipment covered thereby, thus maintaining the sterile condition of the operating room.

6 Claims, 3 Drawing Sheets 5,419,343

ARTHROSCOPY DRAPE AND COLLECTION POUCH

CROSS REFERENCE TO RELATED APPLICATIONS

This application is a continuation of application Ser. No. 07/971,350 filed Nov. 4, 1992, entitled "Improved Arthroscopy Drape and Collection Pouch" by Richard H. Taylor, now abandoned, which is a continuation-in-part of application Ser. No. 07/853,493 filed Mar. 18, 1992 by Richard H. Taylor, and entitled "Improved Arthroscopy Drape and Collection Pouch," now abandoned.

TECHNICAL FIELD OF THE INVENTION

This invention relates generally to surgical drapes. More particularly, but not by way of limitation, this invention relates to an improved arthroscopy drape that aids in maintaining sterile techniques in the operating room.

BACKGROUND OF THE INVENTION

In order to prevent infection in the operating room when performing arthroscopic surgical procedures, it is necessary to follow aseptic draping techniques to avoid the possibility of infecting the patient. More recently, and with the advent of HIV and other infectious viruses, it is also highly desirable to be able to protect the operating room personnel as much as possible from infection by contact with body fluids of infected patients. Accordingly, it is highly desirable to be able to avoid contact with and to collect all waste body fluids that result from an invasive procedure during an operation such as an arthroscopy.

It has been common procedure in operating rooms for many years, to cover the patient with sterilized drapes in all areas except where the operation is being performed. Once the drapes have been placed in position, it is important to the maintenance of the aseptic condition of the operating room that the drapery not be moved from the patient or from covered equipment.

In performing many of the arthroscopic operations, it is necessary that the limb of the patient upon which the operation is being performed be moved to be certain that the proper range of motion is maintained in the effected joint. During such movement, it has been extremely difficult, if not impossible, to prevent movement of the drapery covering the patient. Thus, great care must be exercised to avoid exposing a portion of the operating room equipment or a portion of the patient and thereby violating the required aseptic procedure.

A conventional method for collecting body fluids of a patient undergoing an arthroscopic procedure has been to attach a collection pouch to a surgical drape by an adhesive material. The surgical drape has an opening that allows the limb to penetrate the drape, and the collection pouch has a window and an opening arranged so that the limb can pass through the pouch with the portion to be operated on located at the center of the pouch.

While this design is a great improvement over techniques and apparatuses that existed prior to it, the design and method of using adhesive to secure the collection pouch to the surgical drape has presented problems. During many arthroscopic procedures the limb of the patent must be moved considerably from side to side, and during this movement the collection pouch has moved the drape severely which can violate aseptic technique.

Accordingly, an object of this invention is to provide an improved arthroscopy drape that includes a collection pouch that is securely adhered to a drape panel, but one that permits substantial relative movement of the collection pouch relative to the drape panel without disturbing the position of the drape relative to the patient.

SUMMARY OF THE INVENTION

This invention then provides in one aspect an improved arthroscopy drape comprising a drape panel having a first opening therein and that is sized and arranged to cover the necessary portion of the patient and associated operating apparatus. A resilient material covers the first opening and has its periphery connected to the panel. The resilient material has an aperture therein sized to receive the limb of the patient. An open top collection pouch having a bottom and a window therein which generally corresponds to the opening in the panel, but slightly smaller than the opening, that is connected to the resilient material which covers the opening and arranged so the open top or the collection pouch is located above the limb of the patient. The pouch includes a second opening and has a resilient material covering the second opening. The resilient material in the pouch has an aperture therein for receiving a portion of the limb of the patient.

In another aspect, this invention provides an improved open top collection pouch for use with a drape panel that has a flexible body having a window and an opening therein, a resilient material covers the opening and is arranged to be secured to the drape panel only along the periphery of the window.

BRIEF DESCRIPTION OF THE DRAWINGS

The forgoing and additional objects and advantages of the invention will become more apparent as the following detailed description is read in conjunction with the accompanying drawings wherein like reference characters denote like parts in all views and wherein.

DETAILED DESCRIPTION OF THE INVENTION

Figure 1:
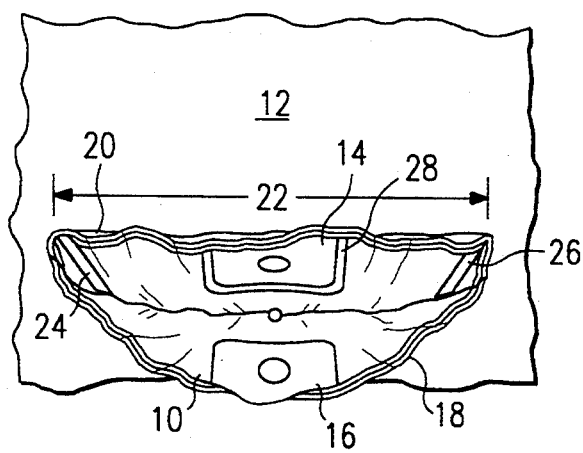
FIG. 1 is a top plan view of a known surgical drape having a collection pouch mounted thereon.

FIG. 1 illustrates a known surgical drape that has a fluid collection pouch 10 connected thereto by an adhesive material to a panel 12 forming part of the drape.

The panel 12 has an opening 14 extending therethrough for receiving a limb of the patient. A second opening 16 is provided in the collection pouch 10 through which the limb can extend to leave the joint that is being operated on located over the collection pouch 10.

The collection pouch 10 is an improvement over apparatus previously used in that it provides the means for collecting essentially all of the body fluids produced during an arthroscopy operation. The upper edge of the collection pouch 10 is provided with a malleable wire 18 that can be formed somewhat as illustrated in FIG. 1 so that the surgeon will have easy access to the joint. In order to be certain that the collection pouch 10 does not become dislodged from the panel 12, adhesive materials were placed along the upper edge 20 of the collection pouch 10 extending entirely across the upper edge of the pouch 10 as illustrated by the dimension line 22. In addition, adhesive strips were placed at 24 and 26 and adhesive strips were placed at 28 encircling the periphery of the opening 14. The collection pouches were securely adhered to the drape 12.

Figure 2:
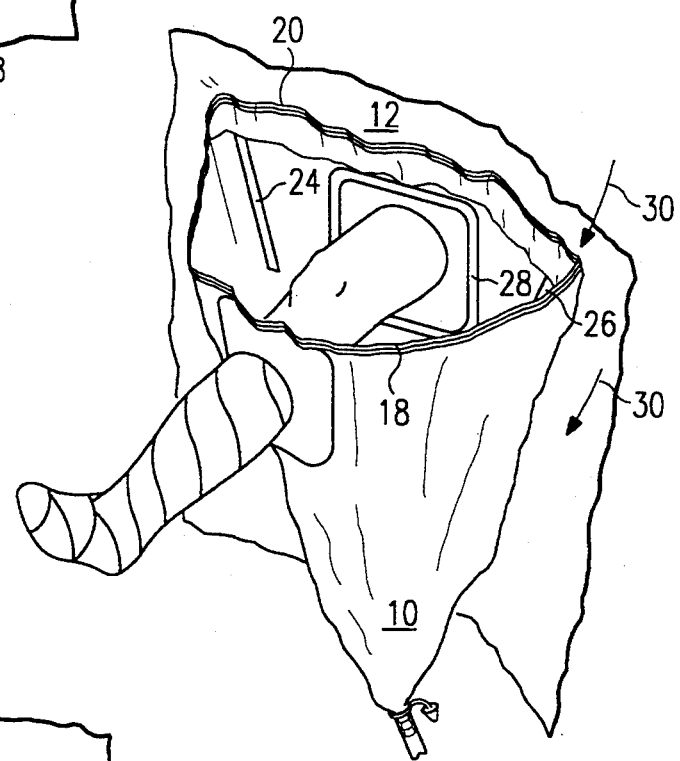
FIG. 2 is a view of the drape of FIG. 1 in a different operating position.

However, and as can be seen in FIG. 2, articulation of the joint to check alignment or range of motion causes the pouch 10 to move severely to one side pulling the drapery panel 12 in the direction of the arrows 30. Thus, while the pouch 10 provides for collection of the body fluids produced during the operation, there is a possibility of uncovering a portion of the patient which was previously draped and thus violating the aseptic condition of the operating room. The present invention helps to alleviate this problem.

Figure 3:
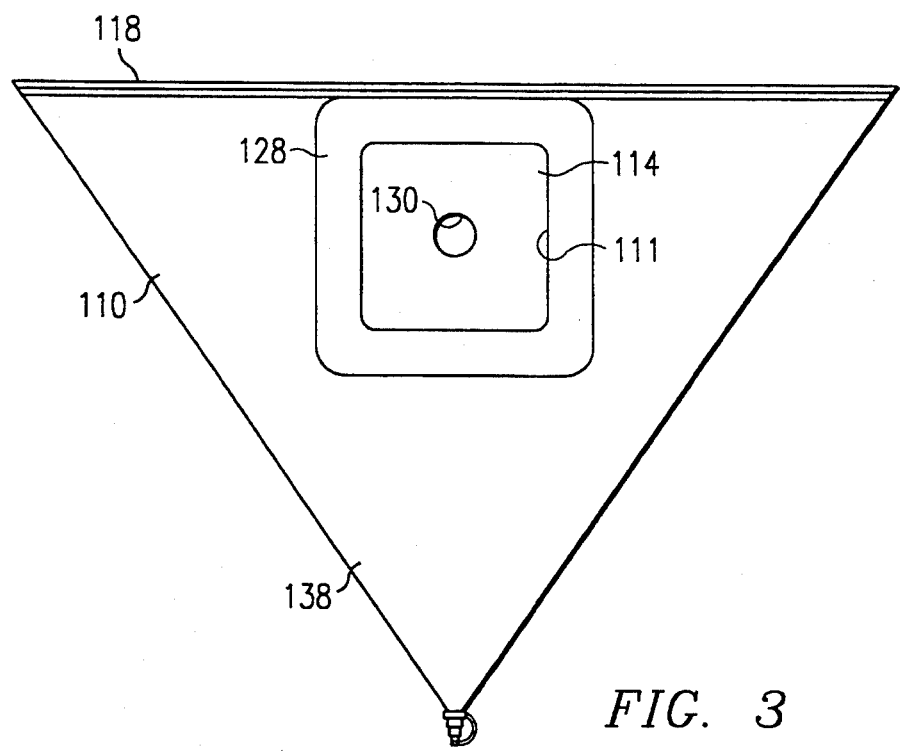
FIG. 3 is a side elevation view of an improved surgical drape that is constructed in accordance with the invention.

Referring to FIGS. 3–6, there is shown therein and generally designated by the reference character 112, an improved arthroscopy drape that is constructed in accordance with the invention. The drape 112 includes panel 113 that is attached to a collection pouch 110. (FIG. 3 is a rear elevation view of only the collection pouch 110.)

Figure 4:
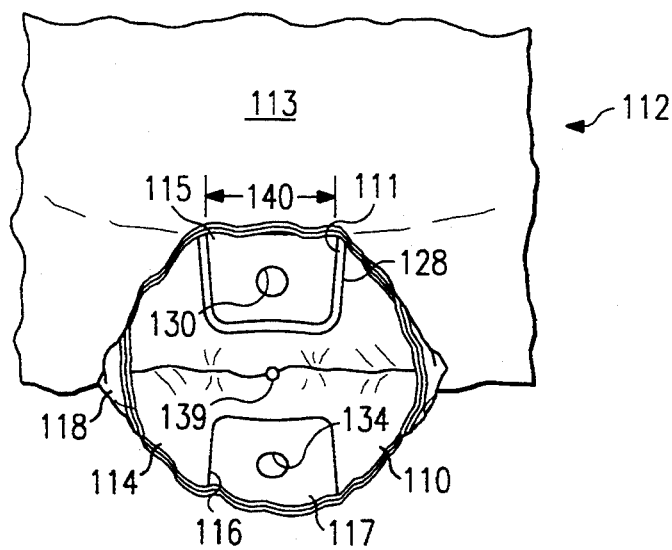
FIG. 4 is a top plan view of the surgical drape of FIG. 3.

Referring to FIG. 4, the drape 112 and pouch 110 are illustrated in a top plan view with the pouch 110 expanded into a generally conical configuration. The pouch 110 has a window 111 formed in a flexible body 114 that overlies a resilient, elastic material 115 that is disposed to cover an opening formed in the drape 112.

A second opening 116 is located directly across the pouch 110 from the window 111. The opening 116 is covered by a resilient material 117 that is adhered, along its peripheral edges, to the pouch 110.

Encircling the upper edge of the collection pouch 110 is a malleable stiffening member 118. The stiffening member 118 is provided so that the pouch 110 in which the body 114 is formed from a flexible yet waterproof material, can be held in a generally conical configuration as is illustrated in FIG. 4.

Figure 5:
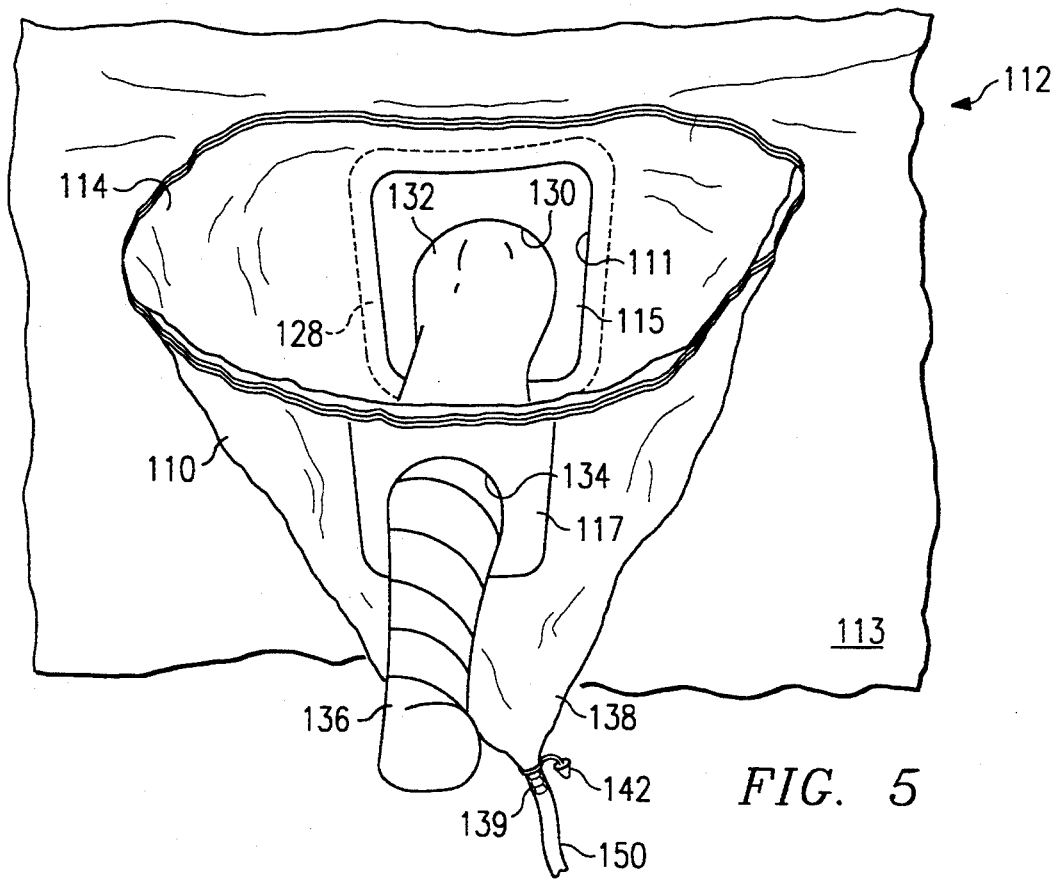
FIG. 5 is a pictorial view of the improved surgical drape of FIG. 3 having a patient's leg extending therethrough with a knee exposed in the collection pouch.

An aperture 130 is formed in the resilient material 115 and is sized to receive a thigh 132 of a patient as is shown in FIG. 5. A second aperture 134 is formed in the resilient material 117 of the pouch 110 and is sized to receive a calf 136 of the patient as illustrated in FIG. 5. At its lower end 138, the collection pouch 110 is provided with a drain tube or opening 140 which is provided with a removable plug 142 for preventing fluid through the drain tube 140 when installed therein.

Referring again to FIG. 4, one means for attaching the collection pouch 110 to the drape panel 113 is shown. It can be seen that the upper edge of the collection pouch 110 is attached to the drape panel 113 along a relatively short dimension line 140, which is generally coextensive with the upper edge of window 111. Adhesive provided along a peripheral edge 128 secures the collection pouch 110 to drape panel 113 about the peripheral edge 128 of the window 111. In lieu of the adhesive, the collection pouch 110 can be welded, fused to or otherwise suitably attached to the drape panel 113.

Figure 4A:
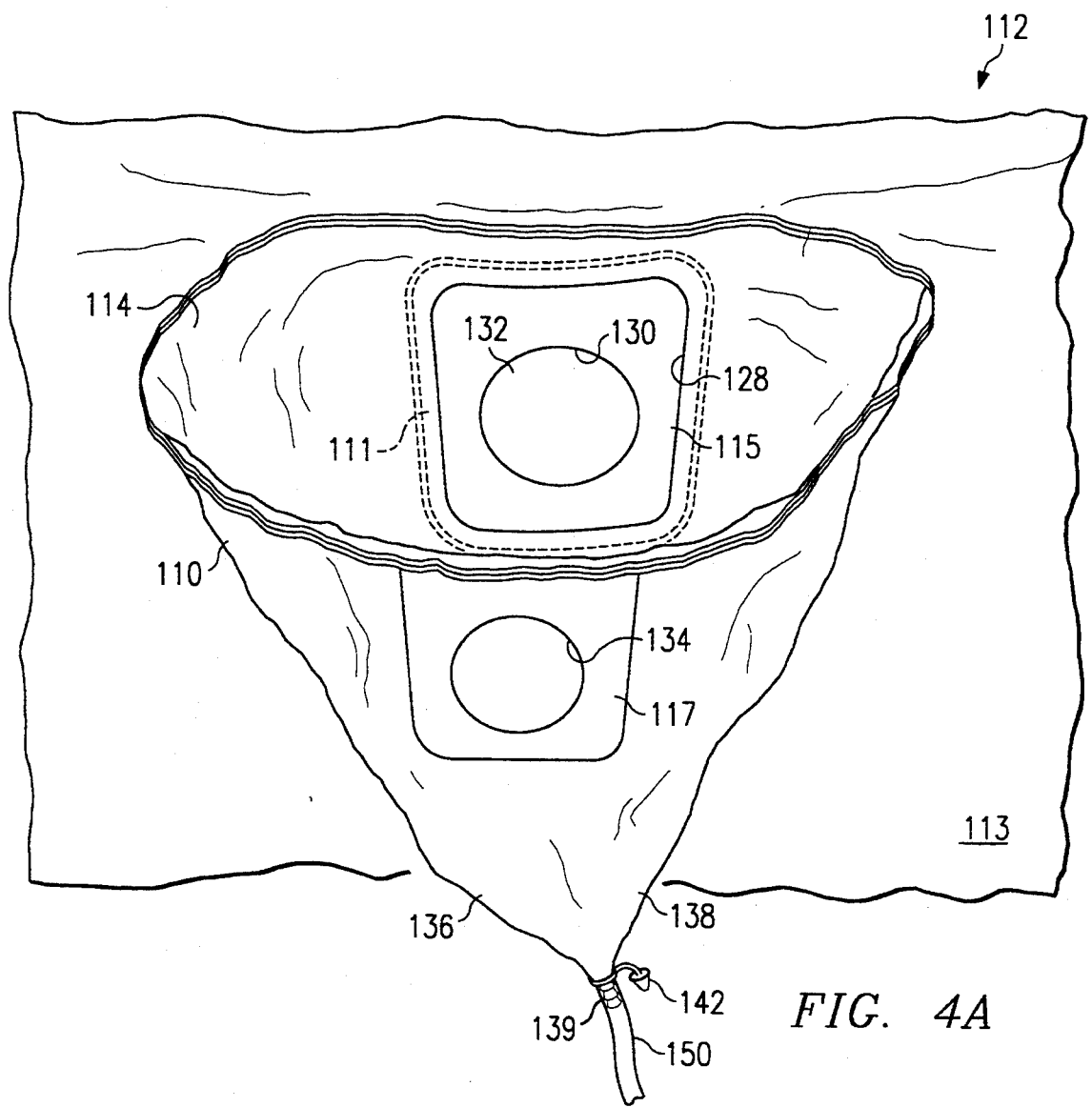
FIG. 4A is a pictorial view of the improved surgical drape of FIG. 3 illustrating another embodiment for connecting the collection pouch to the surgical drape.

Referring now to FIG. 4A, a second means for securing the collection pouch 110 to the drape panel 113 can be seen. The peripheral edge 128 of window 111 is attached to resilient elastic material 115 which thereby secures the pouch 110 to the drape panel 113. This latter method of attachment allows for additional mobility of pouch 110 relative to drape panel 113.

Figure 6:
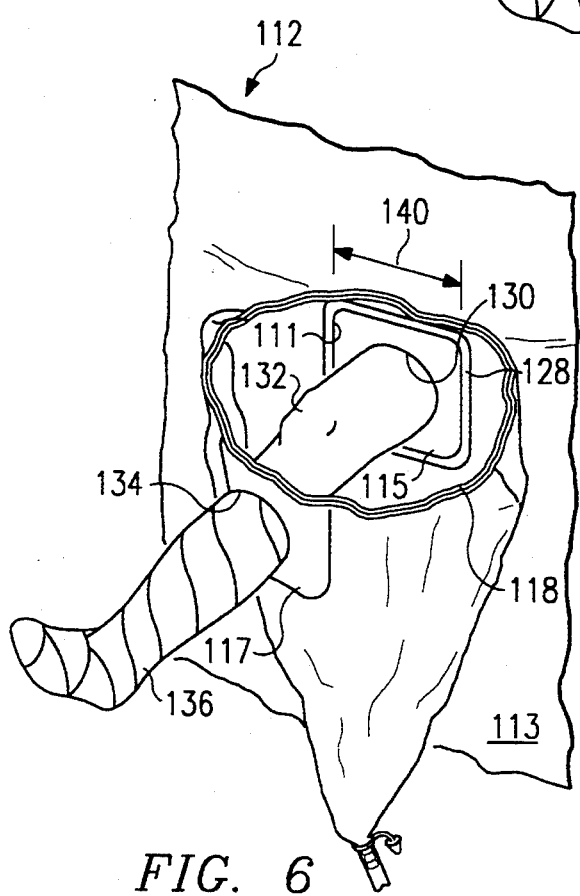
FIG. 6 is a view similar to FIG. 4, but illustrating the improved surgical drape of FIG. 3 in another operating position.

FIGS. 5 and 6 illustrate the use of the drape 112. As shown in those figures, the patient's leg is shown extending through the aperture 130 in the resilient material 115 up to the thigh 132. The calf 136 of the patient extends through the aperture 134 in the resilient material 117 of the collection pouch 110. Thus, the knee of the patient is exposed for the arthroscopic operation. Also in FIG. 5, a tube 150 is shown connected to the drain tube 140 with the closure member 140 removed therefrom to permit the flow of body fluids from the collection pouch 110 through the tube 150.

As previously mentioned, under a first means for attaching the collection pouch 110, the collection pouch 110 is secured or attached to the drapery panel 113 only along the peripheral edge 128 of the window 111 in the pouch 110. Across the top of the pouch 110 the attachment extends only for the distance indicated by the dimension line 140. Accordingly, it can be seen that the attachment of the collection pouch 110 to the panel 113 is along a distance that is less than 10 percent of the periphery of the open end of the collection pouch 110.

With such a small zone of connection, the patient's leg can be moved during the operation as shown in FIG. 6 or through a full range of motion, with little or no movement of the collection pouch 110 being imparted to the panel 113. Thus, the drape 112 with the attached improved collection pouch 110 provides a method of maintaining the sterile environment of the operating room without the danger of moving the drape off of any portion of the patient or off of any apparatus that has been covered thereby.

The substantial difference in attachment between the prior art collection pouch 10 of the drape 12 and the connection of the pouch 110 of this invention of the new drape 112 can clearly be seen by comparing FIGS. 1, 4 and 4A. The effects of articulation or movement of the leg of the patient can be clearly seen by comparing FIGS. 2 and 6. As shown in FIG. 2, the movement to the leg to the left places a load on and does move the drape panel 12 in the direction indicated by the arrows 30. By contrast, articulation of the leg to the left as shown in FIG. 6 has little, if any, effect on the drape 112 due to the small area of connection of the collection pouch 110 to the panel 113.

While the detailed description hereinbefore relates the use of the new surgical drape in connection with the performance of an operation on a patient's knee, it will be understood that the new surgical drape is equally applicable to other arthroscopic procedures.

Further, it will be understood that the embodiments described herein are presented by way of example only and that many changes can be made thereto without departing from the spirit and scope of the invention as defined by the claims.

What is claimed is:

1. An improved arthroscopy drape and collection pouch comprising:
   a drape panel sized and arranged to cover the necessary portion of a patient and associated operating apparatus, said panel having a first opening therein;
   a first resilient material covering said first opening and having its periphery connected to said drape panel, said resilient material having an aperture therethrough sized to receive a limb of the patient;
   said collection pouch having an open top and a window formed in said pouch generally corresponding to said first opening in said panel;
   said pouch connected to said drape panel only by a heat seal between the periphery of said window and said first resilient material;
   said pouch including a second opening with a second resilient material covering said second opening and the periphery of said second resilient material connected to said pouch;
   said second resilient material having an aperture therein for receiving a portion of the limb of the patient;
   said heat seal between the periphery of said window and said first resilient material allowing substantial movement of said pouch relative to said drape panel without disturbing the position of said drape panel relative to said patient when said limb of the patient is disposed within said apertures of said first and second resilient material; and
   said window located relatively below said open top and said window having a width that is less than 25% of the periphery of said open top of said pouch whereby said pouch is relatively moveable in relation to said drape panel except where attached to the periphery of said window and said first resilient material.

2. The drape of claim 1 and also including a malleable stiffening member located in the periphery of said open top for supporting said pouch with the top open providing access to said limb.

3. The drape of claim 2 and also including:
   a drain opening in the lower end of said pouch; and
   a drain plug for permitting and preventing flow through said drain opening.

4. The drape of claim 2 wherein said pouch is generally conical in configuration.

5. The drape of claim 1 and also including:
   a drain opening in the lower end of said pouch opposite from said open top; and
   a drain plug for permitting and preventing flow through said drain opening.

6. The drape of claim 1 wherein said pouch is generally conical in configuration.

* * * * *